United States Patent [19]
Weitzman

[11] 4,138,814
[45] * Feb. 13, 1979

[54] DISPOSABLE DENTAL TRAY FOR TOPICAL APPLICATION OF FLUORIDE GEL AND OTHER DENTAL MEDICATIONS

[75] Inventor: Stewart Weitzman, Portland, Oreg.

[73] Assignee: Pacemaker Corporation, Portland, Oreg.

[*] Notice: The portion of the term of this patent subsequent to May 11, 1993, has been disclaimed.

[21] Appl. No.: 863,216

[22] Filed: Dec. 22, 1977

Related U.S. Application Data

[62] Division of Ser. No. 664,818, Mar. 8, 1976, Pat. No. 4,064,628, which is a division of Ser. No. 529,609, Dec. 5, 1974, Pat. No. 3,955,281.

[51] Int. Cl.² .............................................. A61C 7/00
[52] U.S. Cl. .................................................. 32/14 B
[58] Field of Search .................. 32/14 R, 14 B, 14 E, 32/19; 128/136, 260

[56] References Cited

U.S. PATENT DOCUMENTS

| | | | |
|---|---|---|---|
| 3,224,441 | 12/1965 | Monaghan | 128/136 |
| 3,224,443 | 12/1965 | Monaghan | 128/136 |
| 3,319,626 | 5/1967 | Lindsay | 32/14 B |
| 3,339,547 | 9/1957 | Drabkowski | 128/260 |
| 3,379,193 | 4/1968 | Monaghan | 128/136 |
| 3,399,457 | 9/1968 | Hagman | 32/19 X |
| 3,505,995 | 4/1970 | Greenberg | 32/19 X |

Primary Examiner—Robert Peshock
Attorney, Agent, or Firm—Chernoff & Vilhauer

[57] ABSTRACT

A disposable applicator tray, for topical application of fluoride gel and other dental medications, in the form of an arcuate mouthpiece having a U-shaped cross-section and comprised of flexible polymeric foam material. The interior channeled recess of the tray is anatomically contoured to fit respectively over either of the upper and lower teeth with the walls of the tray contacting the adjacent periodontal tissue. The flexibility of the tray provides a relatively snug seal between the tray perimeter and the periodontal tissue so as to prevent excessive loss of fluoride or other medication contained in the tray and the contamination and dilution thereof with saliva. The applicator tray, which can also serve as a protective mouthpiece for use during athletic activities, is vacuum formed in quantity from a sheet of inexpensive polymeric foam material, thereby permitting it to be economically disposed of after a single use. The bottom surface of the interior recess of the applicator tray, against which the biting edges of the teeth bear when the tray is inserted in the mouth, is provided with indentations anatomically configured to mate with the mouth's dentition pattern and the walls of the tray are similarly anatomically configured so as to provide a comfortable, natural fit and a more thorough and extensive contact of the dental medication with the teeth surfaces.

2 Claims, 4 Drawing Figures

DISPOSABLE DENTAL TRAY FOR TOPICAL APPLICATION OF FLUORIDE GEL AND OTHER DENTAL MEDICATIONS

CROSS-REFERENCES TO RELATED APPLICATIONS

This application is a division of application Ser. No. 664,818 filed Mar. 8, 1976, now U.S. Pat. No. 4,064,628, which in turn was a division of application Ser. No. 529,609 filed Dec. 5, 1974, now U.S. Pat. No. 3,955,281.

BACKGROUND OF THE INVENTION

The present invention relates to a disposable applicator tray, insertable into the mouth as a mouthpiece surrounding respectively either of the upper and lower teeth and adjacent periodontal tissue, for topical application of fluoride gel and other dental medications to the teeth. The tray design, in addition to providing a more comfortable and natural fit in the patient's mouth, produces a relatively snug seal with the adjacent gum tissue so as to better retain and more thoroughly apply the medication to the teeth surfaces and prevent the contamination and dilution of the medication by saliva.

The conventional practice in the prior art is to utilize reusable trays, for topical applications of fluoride gel and other dental medications to the teeth, which are formed of vinyl plastic material and are in the form of an arcuate U-shaped mouthpiece with an open-ended interior recess adapted to loosely fit over either of the upper and lower teeth. The vinyl material utilized is relatively inflexible, thus imparting a high degree of rigidity to the resultant applicator tray which prevents a snug seal of the tray to the adjacent periodontal tissue. Further, the prior art vinyl tray is formed with a regular cross-section and smooth surface finish which precludes a firm seating of the teeth inside the mouthpiece. As a consequence the tray has a tendency to wobble and slide about in the patient's mouth, thus causing a loss of medication, the contamination of the medication with saliva with which it intermixes in the tray, and a very loose contact of the medication with the surfaces of the teeth. Hence the efficacy of the treatment is somewhat diminished.

Moreover, the vinyl material utilized in the fabrication of conventional applicator trays is relatively expensive, thus precluding, on economic grounds, the disposal of the tray after a single use. In order to warrant its expense the vinyl tray must therefore be used numerous times, and to do so necessitates the steps of cold sterilization by soaking in an antiseptic bath and subsequent drying after use to render the tray reusable. Further, because of the rigidity of the vinyl material used, the applicator trays of the prior art do not have the ability to conform to individual variations in the dentition pattern of the patient's mouth. In many situations this inflexibility causes an uncomfortable fit of the tray in the patient's mouth and, in addition, results in excessively large gaps between the edges of the tray and the adjacent teeth and gum tissue so as to allow substantial intermixture of saliva with the fluoride gel or other dental medication and its rapid dilution and drainage away from the teeth surfaces, thereby substantially diminishing the effectiveness of the dental treatment.

SUMMARY OF THE PRESENT INVENTION

In order to overcome the aforementioned significant deficiencies of the reusable vinyl applicator trays of the prior art, the present invention provides a disposable applicator tray, for topical application of fluoride gel and other medications to the teeth, which is of improved design and inexpensive construction, thus promoting both more effective and economical dental treatment. The tray of the present invention is formed of a flexible, polymeric foam material which permits the tray to readily conform to the anatomical configuration of the individual patient's mouth and dentition pattern so as to provide a relatively snug seal between the edges and walls of the tray and the adjacent periodontal tissue and teeth, respectively. In this manner the tray is retained securely against movement and there is relatively little loss of fluoride or other medication by drainage and swallowing and the contamination and dilution of the latter with saliva is substantially retarded. The interior recess of U-shaped cross-section formed in the arcuate tray is configured with indentations along its bottom surface and side walls which anatomically mate with the mouth's dentition pattern. In this manner a comfortable and natural fit of the tray is obtained which reduces the likelihood of the patient's gagging and, more significantly, a thorough and extensive contact of the fluoride gel or other medication with the surfaces of the teeth is achieved.

The foregoing objectives, features and advantages of the present invention will be more readily understood upon consideration of the following detailed description of the invention taken in conjunction with the accompanying drawings.

DETAILED DESCRIPTION OF THE INVENTION

Figure 1:
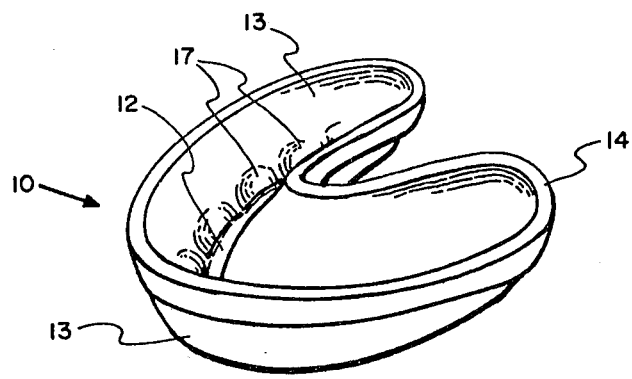
FIG. 1 is a pictorial view of an illustrative embodiment of a dental tray in accordance with the present invention.
Figure 2:
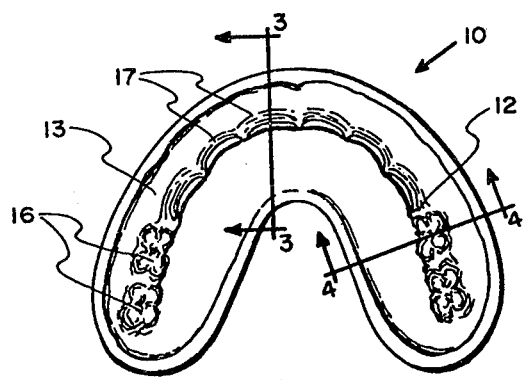
FIG. 2 is a top plan view of the dental tray embodiment.

Referring to FIGS. 1 and 2, the applicator tray of the present invention is in the form of an arcuate mouthpiece 10, anatomically contoured to fit respectively over either of the upper and lower sets of teeth, which is provided with an interior channeled recess 12 of generally U-shaped cross-section. The recess 12 formed in the mouthpiece is walled in along its entire length and ends by a side wall 13 whose upper portion terminates in a perimeter flange portion 14. The base of the interior recess 12 is provided with a plurality of spaced indentations 16 anatomically configured to mate with the dentition pattern of a typical mouth and the interior surface of the side wall 13 is similarly configured. That is, the indentations 16 in the base of the interior channel are generally configured to correspond in location and shape with the biting edges of the teeth and the indentations 17 in the side wall 13 similarly matingly correspond to the vertical surfaces of the teeth when the tray is inserted in the mouth.

The tray, which is of one-piece construction, is comprised of a flexible, non-hydrotropic fine-cell polymeric foam material which is readily moldable to the desired configuration and which is of relatively inexpensive construction so as to warrant its economic disposal after a single use. One material found especially suitable for this application is a cross-linked polyethylene foam having a cell size in the range of 2-3 mils, a density in the range of 1.6-2.4 lbs/ft$^3$, a water absorption factor of 0.1% by volume in a 24 hour period, a tensile strength of 40 psi and an elasticity, measured by percent elongation to fracture, of 275, which is marketed under the trademark MINICEL L-200 by the Foam Division of Haveg Industries, Inc., a subsidiary of Hercules Incorporated, of Wilmington, Delaware. This material has been found to be readily moldable by vacuum die forming from sheet form into an anatomically-shaped mouthpiece tray of the type herein disclosed. The material can be readily cut as desired to adapt the tray to accommodate variations in individual dentition pattern caused by the presence of bridgework, braces, or dental abnormalities. Unlike conventional dental tray material, the very fine cell structure of the MINICEL L-200 foam material renders it substantially non-hydrotropic, as indicated by its low water absorptivity, thus retarding saliva contamination of the fluoride gel or other dental medication contained in the tray.

Figures 3, 4:
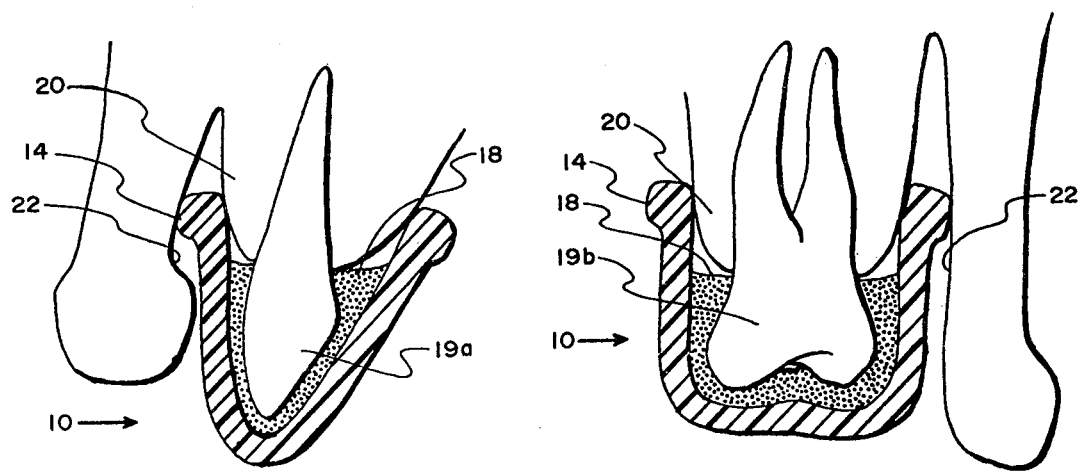
FIG. 3 is a cross-sectional view, taken along the line 3—3 in FIG. 2, of the applicator tray in use.
FIG. 4 is a cross-sectional view, taken along the line 4—4 in FIG. 2, of the applicator tray in use.

The flexibility imparted to the applicator tray by the use of the above-described preferred foam material, in contrast to the rigidity of the conventional vinyl tray, permits the tray to readily conform to the dentition pattern and adjacent gum structure of the individual's mouth in which it is inserted. Thus, as shown in the views of FIGS. 3 and 4 wherein clearances between the tray interior and tooth surfaces are exaggerated for the sake of clarity, the tray 10 is shown applying a medication 18 such as fluoride gel to the exposed surfaces of the anterior and posterior teeth, respectively. In the normal bite of the mouth with the biting edges of the teeth bearing on the interior recess of the tray the flange or lip 14 formed on the perimeter of the walls of the tray is flexed inwardly and brought into contact with the surface of the adjacent periodontal tissue 20 and on the outer side is held there by the pressure of the overlying labial mucosa 22, thus promoting a relatively snug engagement of the applicator tray with the gum and teeth surfaces and producing thereby the beneficial results hereinbefore described.

The tray of the present invention also finds application as a safety mouthpiece, economically disposable after a single or limited use, in protecting the teeth of athletic participants since, in addition to the natural comfortable fit obtained by virtue of its anatomical configuration, the compressive strength of the MINICEL L-200 material, ranging from 3 psi at 10% deflection to 14 psi at 50% deflection, well cushions the teeth from the consequences of severe impacts.

The terms and expressions which have been employed in the foregoing abstract and specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A disposable applicator tray for topical application of fluoride gel and other dental medications to the teeth, said tray consisting essentially of an arcuate unitary member molded from flexible, non-hydrotropic, fine-cell polymeric foam material and having bottom and wall surfaces forming a channeled interior recess of generally U-shaped cross-section configured to fit over either of the upper or lower teeth of the mouth, the perimeter of said tray wall being provided with a thickened flange portion, whereby a comfortable, non-gagging fit of the tray inside the mouth is obtained with said flanged perimeter of the walls of the tray being flexed by the bite of the mouth to contact the adjacent periodontal tissue to thereby provide a snug seal therewith and prevent the contamination and dilution by saliva of medication contained in said tray.

2. The applicator tray of claim 1 wherein said polymeric foam material is a cross-linked polyethylene foam having a cell size in the range of 2-3 mils, a density in the range of 1.6-2.4 lbs/ft$^3$, a water absorption factor of about 0.1% by volume in a 24-hour period, a tensile strength of about 40 psi, an elasticity, measured by percent elongation to fracture, of about 275, and a compressive strength ranging from about 3 psi at 10% deflection to about 14 psi at 50% deflection.

* * * * *